(12) United States Patent
Gregory et al.

(10) Patent No.: US 11,191,721 B1
(45) Date of Patent: Dec. 7, 2021

(54) PARTICLE DELIVERY VIA SMALL-SCALE MORPHOLOGY MATERIALS FOR ANTIBACTERIAL APPLICATIONS

(71) Applicants: Jessica M. Gregory, Butte, MT (US); Jack L. Skinner, Butte, MT (US); Marisa L. Pedulla, Butte, MT (US); M. Katie Hailer, Butte, MT (US)

(72) Inventors: Jessica M. Gregory, Butte, MT (US); Jack L. Skinner, Butte, MT (US); Marisa L. Pedulla, Butte, MT (US); M. Katie Hailer, Butte, MT (US)

( * ) Notice: Subject to any disclaimer, the term of this patent is extended or adjusted under 35 U.S.C. 154(b) by 0 days.

(21) Appl. No.: 16/421,108

(22) Filed: May 23, 2019

Related U.S. Application Data

(63) Continuation-in-part of application No. 15/166,192, filed on May 26, 2016, now Pat. No. 10,392,612.
(Continued)

(51) Int. Cl.
| | |
|---|---|
| *A61K 9/00* | (2006.01) |
| *A61K 9/70* | (2006.01) |
| *A61K 35/76* | (2015.01) |
| *C12N 7/00* | (2006.01) |
| *A61K 47/02* | (2006.01) |
| *A61K 47/34* | (2017.01) |
| *A01N 25/34* | (2006.01) |

(Continued)

(52) U.S. Cl.
CPC ............ *A61K 9/0092* (2013.01); *A01N 25/10* (2013.01); *A01N 25/34* (2013.01); *A01N 63/00* (2013.01); *A23L 3/34635* (2013.01); *A61K 9/70* (2013.01); *A61K 35/76* (2013.01); *A61K 47/02* (2013.01); *A61K 47/34* (2013.01); *C12N 7/00* (2013.01); *D01D 5/0007* (2013.01); *A23V 2002/00* (2013.01); *C12N 2795/00031* (2013.01); *C12N 2795/00032* (2013.01)

(58) Field of Classification Search
None
See application file for complete search history.

(56) References Cited

U.S. PATENT DOCUMENTS

2013/0196405 A1* 8/2013 Singh .................. D01D 5/0007
435/182

* cited by examiner

*Primary Examiner* — Jeffrey D Washville
(74) *Attorney, Agent, or Firm* — Haffey Vap PLLC; Mitchell J. W. Vap

(57) ABSTRACT

Disclosed herein is a particle delivery system comprising electrospun nanofiber comprised of coaxial fiber with a microfluidic core. Iron-doped apatite nanoparticles (IDANPs) have demonstrated a unique influence over phage killing of bacteria, whereby, IDANP-exposed bacterial cultures experience 2× the bacterial death as controls. IDANPs consist of hydroxyapatite (HA) doped with iron. HA is a mineral known to be biocompatible and analogous to the inorganic constituent of mammalian bone and teeth and has been approved by the Food and Drug Administration (FDA) for many applications in medicine and dentistry. Previous work has shown that for IDANPs to enhance antibacterial activity of phage to the greatest extent, bacterial cultures should be exposed to IDANPs for 1 hr prior to phage introduction. Biocompatible polymer materials which encase IDANPs and/or phage can be used to disseminate IDANPs and/or phage in a controlled manner into a physiological system for treatment of bacterial infection. When components of said materials contain micro- or nano-scale components, high surface-to-volume ratio for treatment delivery is garnered.

15 Claims, 11 Drawing Sheets

Related U.S. Application Data

(60) Provisional application No. 62/166,392, filed on May 26, 2015, provisional application No. 62/675,425, filed on May 23, 2018.

(51) Int. Cl.
| | |
|---|---|
| *A01N 25/10* | (2006.01) |
| *A23L 3/3463* | (2006.01) |
| *D01D 5/00* | (2006.01) |
| *A01N 63/00* | (2020.01) |

FIG. 10
FIG. 11
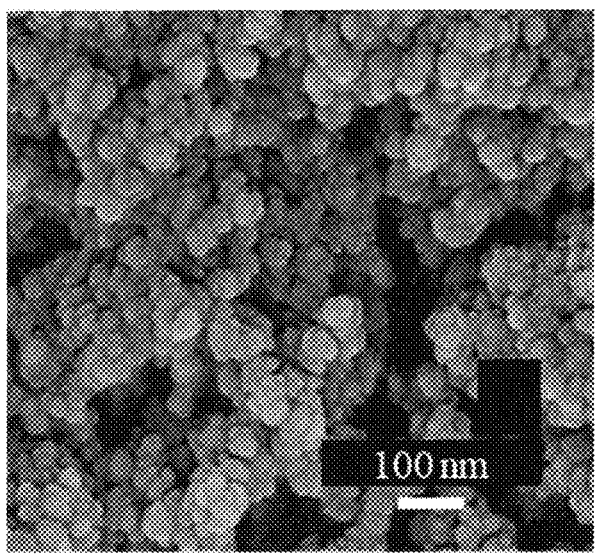 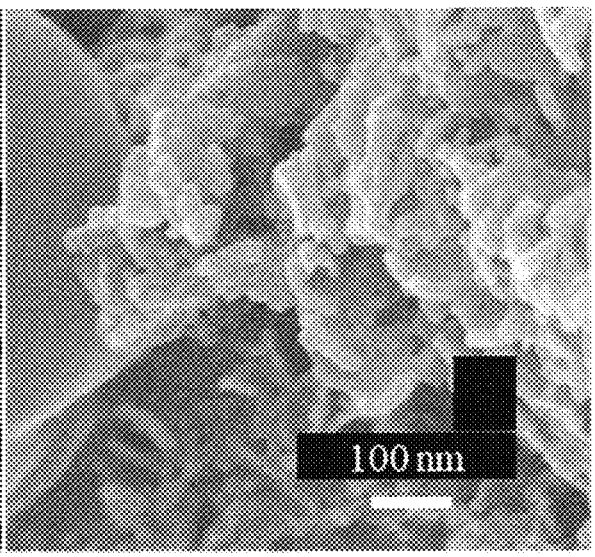

FIG. 12
FIG. 13
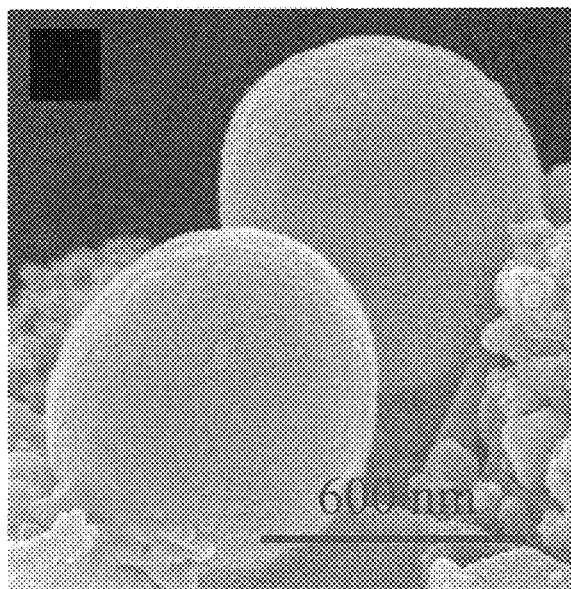
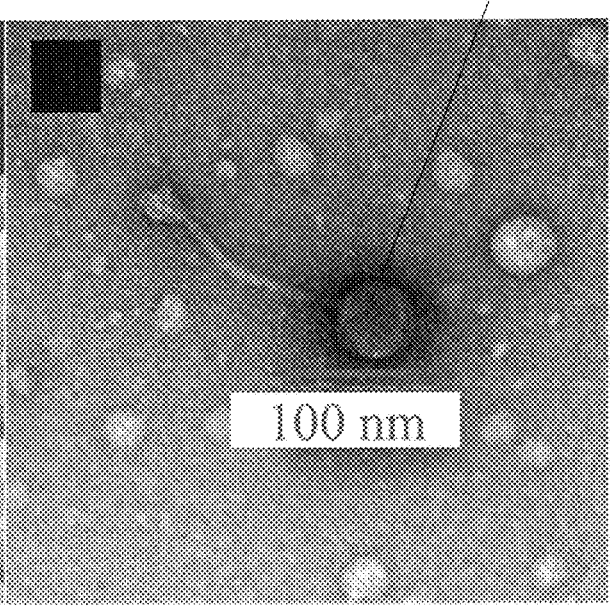

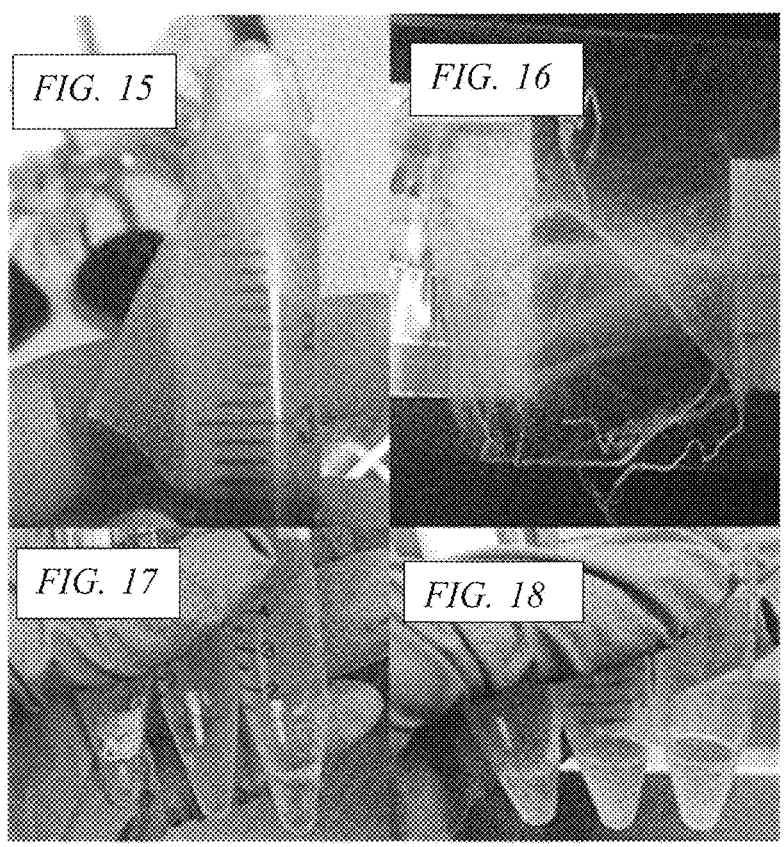

FIG. 19
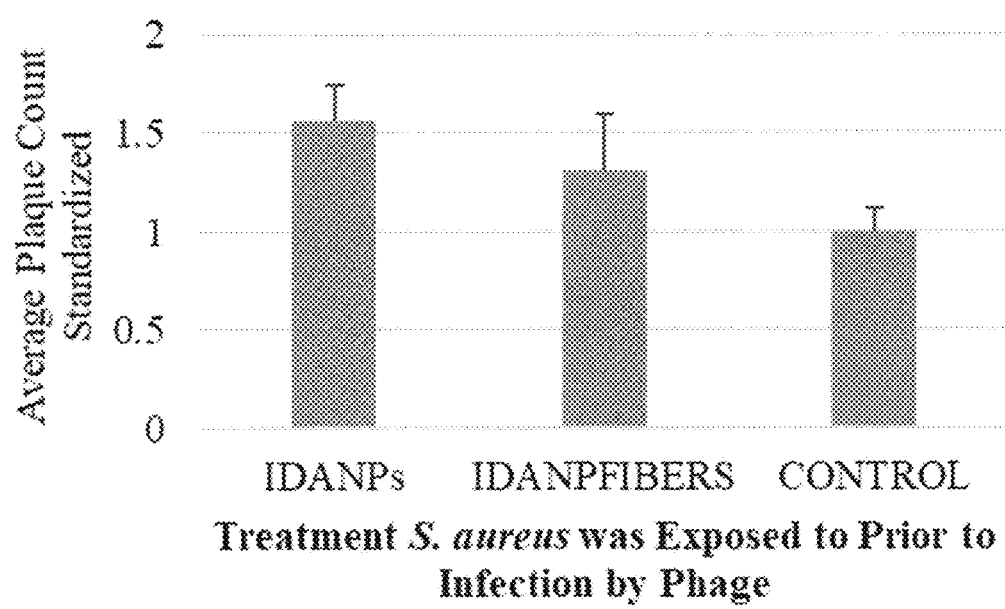
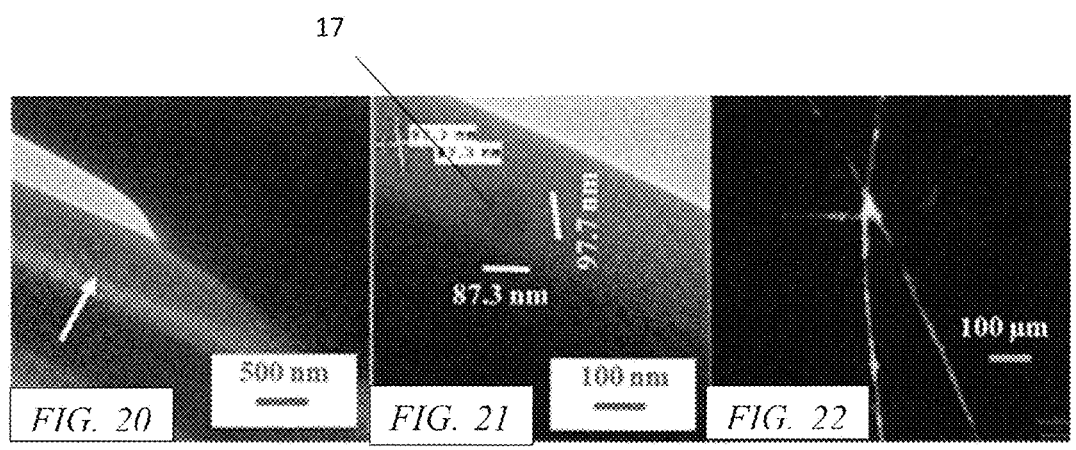
FIG. 20　　FIG. 21　　FIG. 22

US 11,191,721 B1

PARTICLE DELIVERY VIA SMALL-SCALE MORPHOLOGY MATERIALS FOR ANTIBACTERIAL APPLICATIONS

CROSS-REFERENCE TO RELATED APPLICATIONS

This continuation-in-part application claims the benefit of U.S. Non-provisional application Ser. No. 15/166,192, filed on May 26, 2016, which claims the benefit of U.S. Provisional Application No. 62/166,392, filed on May 26, 2015. This continuation-in-part application also claims the benefit of U.S. Provisional Application No. 62/675,425, filed on May 23, 2018, the disclosures of which are hereby incorporated by reference in their entirety including all figures, tables and drawings.

STATEMENT REGARDING FEDERALLY SPONSORED RESEARCH OR DEVELOPMENT

This invention was made with government support under EAGER Grants #1338478 and 13384789 awarded by the National Science Foundation. The government has certain rights in this invention.

THE NAMES OF THE PARTIES TO A JOINT RESEARCH AGREEMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

Targeted delivery has allowed man to manipulate life on a cellular level. Life saving chemotherapy and radiation can be delivered to diseased cells while sparing healthy cells. Genes can be manipulated within a cell by the intra-cellular delivery of bacteriophages and vectors. Antibiotic and vaccine therapy delivery can be enhanced by delivering drugs to a cell with an adjuvant.

While methods of transporting and delivering these particles to a cell is ever evolving there remains a need for transport methods and materials that efficiently and effectively deliver particulate material to cells.

It is well known that bacterial strains have become increasingly resistant to traditional antibiotic therapies, prompting critical research and development of alternatives. The Centers for Disease Control and prevention estimate that at least 2 million people in the United States become infected with antibiotic-resistant bacteria, and at least 23,000 people die each year as a direct result of those infections [*Antibiotic Resistance Threats in the United States* 2013, (U.S. Department of Health and Human Services, Centers for Disease Control and Prevention 2013), pp. 11-12]. As an alternative to traditional antibiotics, bacterial viruses (phages) capable of exponential bacterial destruction have been used. Phages kill bacteria through biological processes that differ from traditional antibiotics and therefore can avoid bacterial resistance. Phage therapy was studied initially approximately 87 years ago in humans [F. d'Herelle, B. New York Acad. Med. 7, 329 (1931)] and has demonstrated minimal side effects [I. U. Haq, W. N. Chaudhry, M. N. Akhtar, S. Andleeb, and I. Qadri, Virol. J. 9, (2012)] while remaining an effective antibiotic treatment for many applications ranging from diabetes-related infection to preventing immune responses associated with artificial implants [S. Chhibber, T. Kaur, and S. Kaur, PloS One 8, (2013), J. J. Mendes, C. Leandro, S. Corte-Real, R. Barbosa, P. Cavaco-Silva, J. Melo-Cristino, A. Gorski, and M. Garcia, Wound Repair Regener. 21, 595 (2013), M. P. Lungren, D. Christensen, R. Kankotia, I. Falk, B. E. Paxton, and C. Y. Kim, Bacteriophage 3, (2013), C. Yilmaz, M. Colak, B. C. Yilmaz, G. Ersoz, M. Kutateladze, and M. Gozlugol, J. Bone Jt. 95, 117 (2013), R. Międzybrodzki, W. Fortuna, B. Weber-Dąbrowska, and A. Górski, Postepy. Hig. Med. Dosw. 61, 461 (2007)]. Phage isolation is fast, simple, inexpensive, and resistance to phage develops about ten times slower than antibiotic resistance [S. Parasion, M. Kwiatek, R. Gryko, L. Mizak, A. Malm, Pol. J. Microbiol. 63, 137 (2014)]. Such qualities indicate that phage therapy may require fewer or limited administrations compared to traditional antibiotics [J. Doss, K. Culbertson, D. Hahn, J. Camacho and N. Barekzi, Viruses 9, (2017)]. Phage have high specificity for their bacterial hosts, alleviating concern of phage harming the natural microbiota or infecting mammalian cells [S. Parasion, M. Kwiatek, R. Gryko, L. Mizak, A. Malm, Pol. J. Microbiol. 63, 137 (2014)].

A nanoparticle adjuvant has been characterized which significantly enhances phage killing of bacteria [J. M. Andriolo, R. M. Hensleigh, C. A. McConnell, M. Pedulla, K. Hailer, R. Kasinath, G. Wyss, W. Gleason, and J. L. Skinner, J. Vac. Sci. Technol. B 32, (2014), J. M. Andriolo, R. J. Rossi, C. A. McConnell, B. I. Connors, K. L. Trout, M. K. Hailer, and J. L. Skinner, J. Vac. Sci. Technol. 15, 908 (2016)]. Iron-doped apatite nanoparticles (IDANPs) are composed of calcium, phosphate, and hydroxyl ions and resemble hydroxyapatite, a mineral well known to be biocompatible and analogous to the inorganic constituent of mammalian bone and teeth [L. C. Palmer, C. J. Newcomb, S. R. Kaltz, E. D. Spoerke, and S. I. Stupp, Chem. Rev. 108, 4754 (2008)]. Substituted hydroxyapatites have been used in a variety of biomedical applications approved by the Food and Drug Administration [M. Šupová, Ceram. Int. 41, 9203 (2015)], including drug delivery [V. S. Prem and S. Chandra, J. Biomater Tissue Eng. 2, 269 (2012), P. Sandev, S. Podaralla, R. S. Kaushik, and O. Perumal, J. Biomed. Nanotechnol. 9, 132 (2013)], gene delivery [D. Lee, K. Upadhye, and P. N. Kumta, Mater. Sci. Eng. B 177, 269 (2012)], biocomposite materials, scaffolds for stem cells [A. K. Keshri and A. Agarwal, Nanosci. Nanotechnol. Let. 4, 228 (2012)], bone implantation coatings [A. K. Keshri and A. Agarwal, Nanosci. Nanotechnol. Let. 4, 228 (2012)], and cancer growth inhibition [S. Ezhaveni, R. Yuvakkumar, M. Rajkumar, N. M. Sundaram, and V. Rajendran, J. Nanosci. Nanotechnol. 13, 1631 (2013)]. When pre-exposed to IDANPs, bacteria have demonstrated an increased susceptibility to death by phage up to 2.3 times that of controls [J. M. Andriolo, R. M. Hensleigh, C. A. McConnell, M. Pedulla, K. Hailer, R. Kasinath, G. Wyss, W. Gleason, and J. L. Skinner, J. Vac. Sci. Technol. B 32, (2014)]. IDANP-enhanced phage killing has been demonstrated with gram-positive and gram-negative strains of bacteria, as well as with the use of DNA and RNA phages, and phages with contractile and non-contractile tails [J. M. Andriolo, R. M. Hensleigh, C. A. McConnell, M. Pedulla, K. Hailer, R. Kasinath, G. Wyss, W. Gleason, and J. L. Skinner, J. Vac. Sci. Technol. B 32, (2014)]. While studying the effect of IDANP-enhanced bacterial death by phage, one study showed that bacteria should be exposed to IDANPs 1 hr prior to phage introduction for maximum effect [J. M. Andriolo, G. F. Wyss, J. P. Murphy, M. L. Pedulla, M. K. Hailer, and J. L. Skinner, M R S Advances 2, 2465 (2017)]. Using scanning electron microscopy (SEM), we observed that over the 1 hr time period, IDANPs coat the surface of bacterial cells. At 1 hr, bacteria are almost completely coated with IDANPs. Although it has not been confirmed, we hypothesize that while the initial interaction of IDANPs and the bacterial surface result in increased bacterial susceptibility to infection, complete coverage of the bacterial surface with nano-sized particles may result in a physical barrier that prevents maximum phage infectivity.

The 1 hr ideal exposure time demonstrates that IDANP-assisted phage therapy would not be straight forward but would instead require controlled time release of IDANPs and phage. These findings motivated the design of an electrospun nanofiber mesh treatment delivery system that allows burst release of IDANPs, followed by slow, consistent release of phage for treatment of topical bacterial infections. The composite nanofiber mesh we designed for IDANP-assisted phage therapy treatment of topical wounds consists of a superficial, rapid release layer of polyethylene oxide (PEO) fibers doped with IDANPs, followed by deeper, coaxial polycaprolactone/polyethylene glycol (PCL/PEG) blended polymer fibers for slower phage delivery. Previous investigations established that IDANP-doped PEO fibers are effective vehicles for dissemination of IDANPs for bacterial exposure and resultant increased bacterial death by phage [J. M. Andriolo, G. F. Wyss, J. P. Murphy, M. L. Pedulla, M. K. Hailer, and J. L. Skinner, M R S Advances 2, 2465 (2017)]. In more recent work, the second part of the composite treatment mesh was fabricated, in which blended polymer fibers were electrospun into core-shell structured fibers filled with a microfluidic channel containing phage for dissemination of the phage over time [J. M. Andriolo, N. J. Sutton, J. P. Murphy, L. G. Huston, E. A. Kooistra-Manning, R. F. West, M. L. Pedulla, M. K. Hailer, and J. L. Skinner, Submitted to MRS Advances for Publication, Apr. 18, 2018]. Blending of PCL/PEG provided an adequate material for controlled phage release over time. IDANP-filled fibers and phage-filled fibers were tested for successful release using in vitro, plaque assay methods.

Bacterial viruses (phage) and human viruses have many similarities including structure and mechanism of infection. To ensure safety of IDANPs in a human system, it had to be established that while these nanoparticles (NPs) increased phage infection and killing of bacterial cells, that IDANPs did not also increase eukaryotic virus infections and killing of eukaryotic cells. To test IDANP-effect on eukaryotic virus infection of eukaryotic cells, experiments were carried out using *Chlorella variabilis* NC64A (NC64A) and its virus, Paramecium bursaria chlorella virus 1 (PBCV-1) [Andriolo et al., *IEEE Transactions on Nanobioscience*, 2016]. Results indicated that in an algal system, viral infections were not increased or decreased by the addition of IDANPs.

All patents, patent applications, provisional patent applications and publications referred to or cited herein, are incorporated by reference in their entirety to the extent they are not inconsistent with the teachings of the specification.

BRIEF SUMMARY OF THE INVENTION

The invention involves particle delivery via small-scale morphology materials, wherein the small-scale morphology materials have micro- or nano-scale features and/or are of micro- or nano-size entirely. The small scale morphology materials are of partial or complete synthetic nature, are made up in part or completely of polymer and/or polymer composite, and fabricated for the purpose of particulate delivery, movement, transfer, transport, or release from either the external or any more interior material surface to either living or non-living systems or artificial representations thereof.

IDANPs are synthesized using wet chemical precipitation methods [Andriolo et al., *Journal of Vacuum Science and Technology B*, 2013 & Andriolo et al., *IEEE Transactions on Nanobioscience*, 201]). Synthesis of IDANPs involves iron replacement of calcium in the apatite unit cell to 30% iron in the molar ratio of total iron plus calcium. Citrate was used as a capping agent to arrest NPs at the nanoscale. The reaction formula is as follows:

7Ca(OH)2+3FeCl3+6KH2PO4 Citric Acid Ca7Fe3 (PO4)6(OH)2+6KOH+12H2O+9Cl—

During synthesis of 30% IDANPs with 1× citrate, a 500 mL flask held at 25° C. was filled with 200 mL deionized water and stirred by stir bar as the following reagents were added in the order listed:

0.260 g Calcium Hydroxide (Ca(OH)2)
  0.243 g Iron Chloride (FeCl3)
  0.263 g Citric Acid Anhydrous (C6H7O7)
  0.408 g monopotassium phosphate (KH2PO4) that was pre-dissolved in 50 mL deionized water is added dropwise over a period of 1 minute.

The final solution was measured at a pH of approximately 4.5 and brought up to a pH of 7.5 using 1 M NaOH. IDANPs were then stirred at 25° C. for seven days. After seven days, IDANPs were centrifuged for 30 min at 2000 rpm. IDANP supernatant was then removed, leaving the IDANP pellet. The pellet was washed 2λ with sterile, deionized water (18 MΩ), and IDANPs were re-suspended in deionized water before being sterilized in an autoclave for 40 minutes. IDANP concentration resulting from this synthesis procedure was estimated to be 1.54 mg/mL by simple drying method and weighing of dried IDANPs.

Results of in vitro experiments coupled with approval by the FDA for use of hydroxyapatite materials in biomedical applications, indicate that IDANPs would be useful adjuvants for phage therapy in mammalian systems. Based on these findings, IDANPs delivered in conjunction with phage would provide significant enhancement of phage therapies which serve as alternative therapies to traditional antibiotics. Due to the finding that IDANPs and phage delivered on a specific time scale act as the most effective antibacterial treatment, controlled release of IDANPs and phage can be performed using polymer materials which dissolve in a physiological system. Fabrication of IDANP- and phage-filled polymer materials has been demonstrated using various forms of polymer encapsulation. IDANP- and phage-filled small-scale and biocompatible polymer materials which contain at least one component with a dimension below 100 μm, can be formed into various forms of fibers or capsules. On the macroscale, materials produced would have high surface-to-volume ratio and be dissolvable in physiological systems. When IDANP-filled and/or phage-filled polymer materials are combined in a composite material or used individually, superior phage therapy treatment delivery systems used to supplement or treat mammalian bacterial infections can be fabricated.

BRIEF DESCRIPTION OF THE SEVERAL VIEWS OF THE DRAWINGS

FIG. 10 shows IDANPs synthesized at 25° C., with 30% iron-doping, and 5.5 mM citrate. IDANPs show spherical morphology with particle diameters ranging from 20-50 nm.

FIG. 11 shows IDANP's synthesized at 25° C. with 30% iron-doping, and no citrate. Lack of citrate during preparation resulted in IDANP elongation FIG. 12 shows *Staphylococcus aureus* (ATCC® 337420 used during plaque assays.

FIG. 13 shows phage used during plaque assays discovered on dairy cow hair samples at Montana State University, and isolated on methicillin-resistant *S. aureus* strain USA300.

FIG. 15 PEO doped with IDANPs prior to ES.

FIG. 16 Electrospun PEO mesh doped with IDANPs.

FIG. 17 Staphylococcal treatments prior to the addition of bacteria.

FIG. 18 Staphylococcal treatments after bacteria grown in media was added.

FIG. 19 Plaque assay results standardized from 2 experiments, showing the effectiveness of each treatment to enhancement of phage infectivity.

FIG. 20 TEM of coaxial, electrospun PCL fibers containing phage.

FIG. 21 TEM of coaxial, electrospun PCL fiber containing phage. Fibers contained octahedral shapes, consistent with phage head morphology and size.

FIG. 22 EFM of phage tagged with fluorescent dye inside coaxial, electrospun PCL fibers.

DETAILED DESCRIPTION OF THE INVENTION

The invention involves small-scale materials which facilitate either passively or by external manipulation the transport of particles from the material to living or non-living systems. The small scale morphology materials of the subject invention are of partial or complete polymer and/or polymer composite composition and may contain multiple materials. Features of these materials or the materials in their entirety are less than 100 micron in at least one dimension.

The small-scale morphology materials of the subject invention are micro- and nano-scale size materials or have either micro- and/or nano scale features. Micro- or nano-scale refers to the materials or features being from about 0 to about 100 microns and less than about 100 microns. Size refers to either diameter, and/or circumference, and/or perimeter, and/or volume of the subject material or of a material feature.

The small scale morphology materials of the subject invention can either comprise components or be comprised entirely of fiber/s or transport vesicle/s or vessel/s or transport particle/s or a combination thereof including a combination with or without fibers. The subject materials can be made as a single layer, multiple layers, a composite, or be a colloid. The micro- and/or nano-scale materials can have organic and/or inorganic components or can be of an entire synthetic composition by way of either construction, and/or fabrication, and/or chemical synthesis, and/or preparation, and/or assembly. These micro- and/or nano-scale materials can likewise be of partial or complete polymer and/or polymer composite material. The synthetic nature of small scale morphology materials are either fabricated, and/or chemically synthesized, and/or prepared, and/or assembled. It is noted however that not all components of these materials may be of synthetic nature and materials may contain a combination of synthetic and organic, or non-synthetic, materials.

Figure 1:
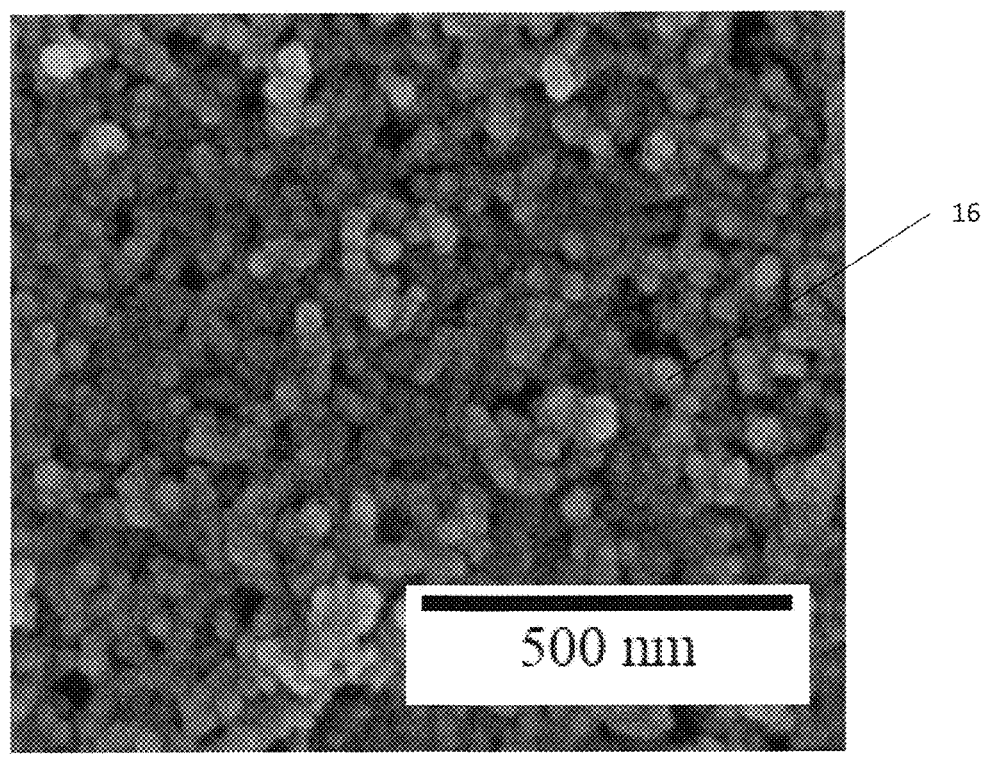
FIG. 1 is a scanning electron micrograph of a particulate that could be transported via the small-scale morphology material of the subject invention.
Figure 2:
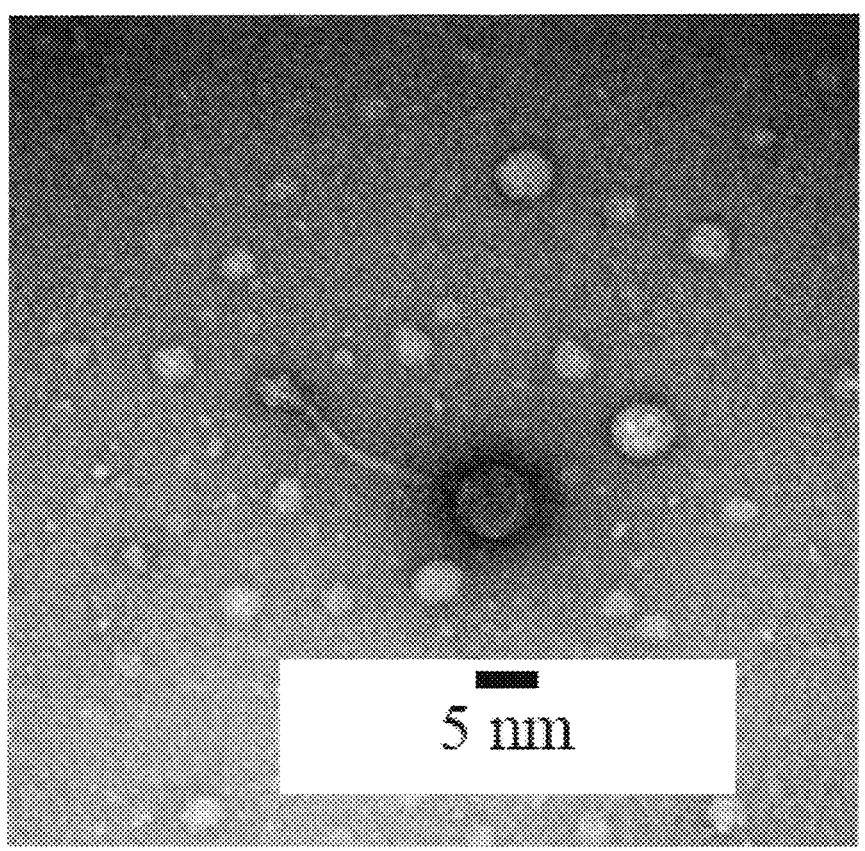
FIG. 2 is a transmission electron micrograph of virus that could be transported via the small-scale morphology material of the subject invention.
Figure 3:
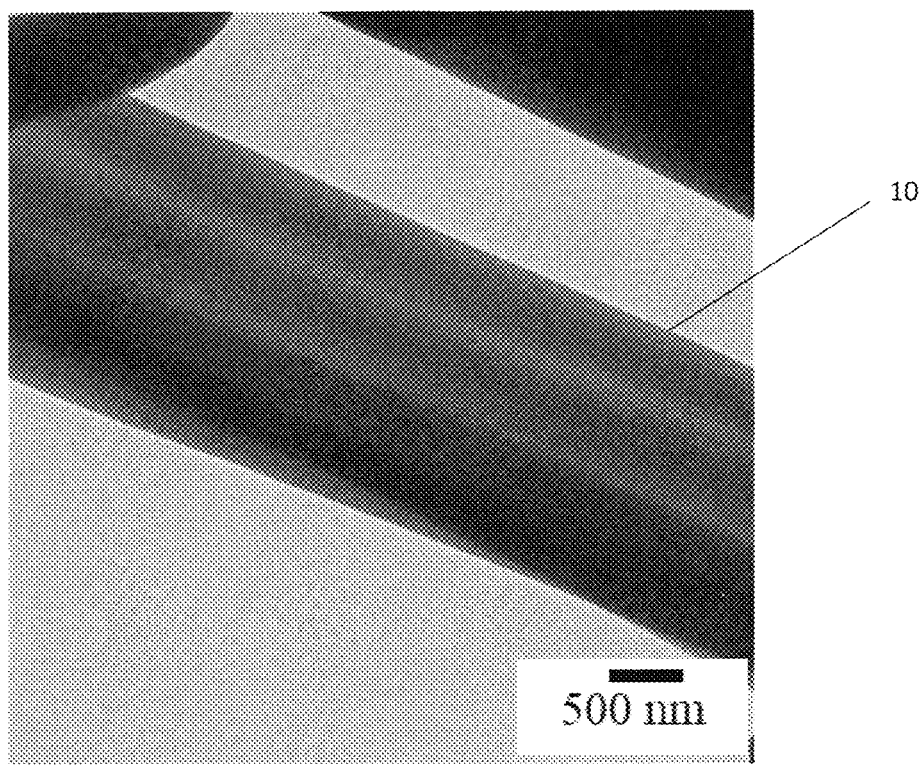
FIG. 3 is a transmission electron micrograph of a preferred embodiment of the small-scale morphology material of the subject invention that are coaxial or core-sheath fibers.
Figure 4:
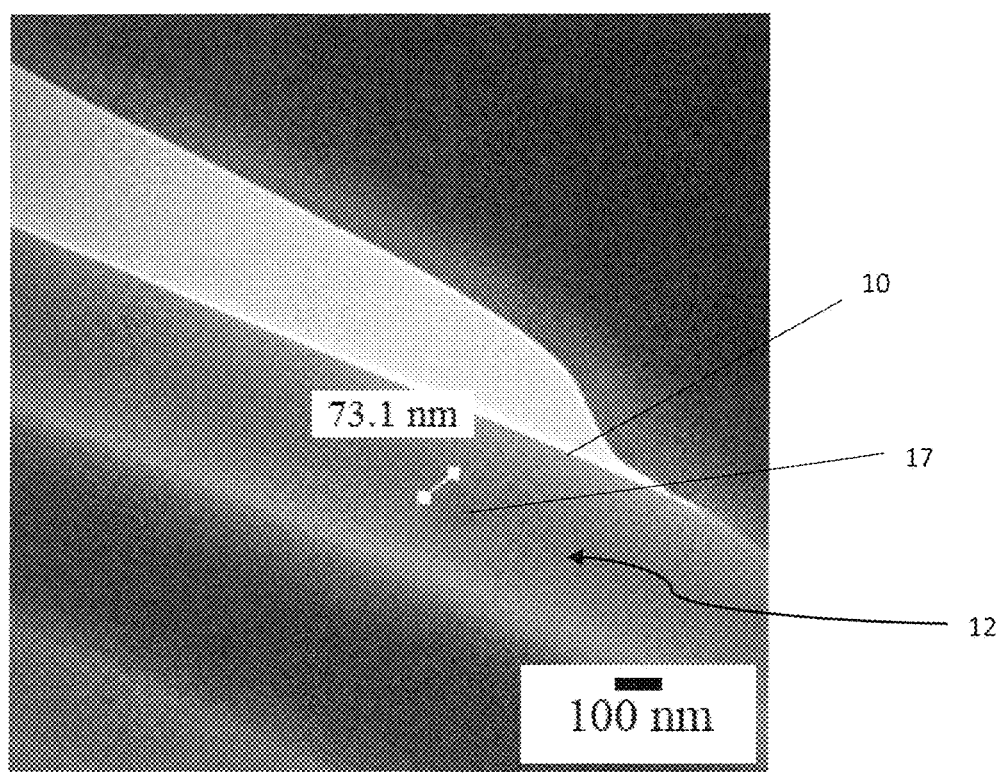
FIG. 4 is a transmission electron micrograph of the preferred embodiment of coaxial or core-sheath fibers containing a virus.
Figure 5:
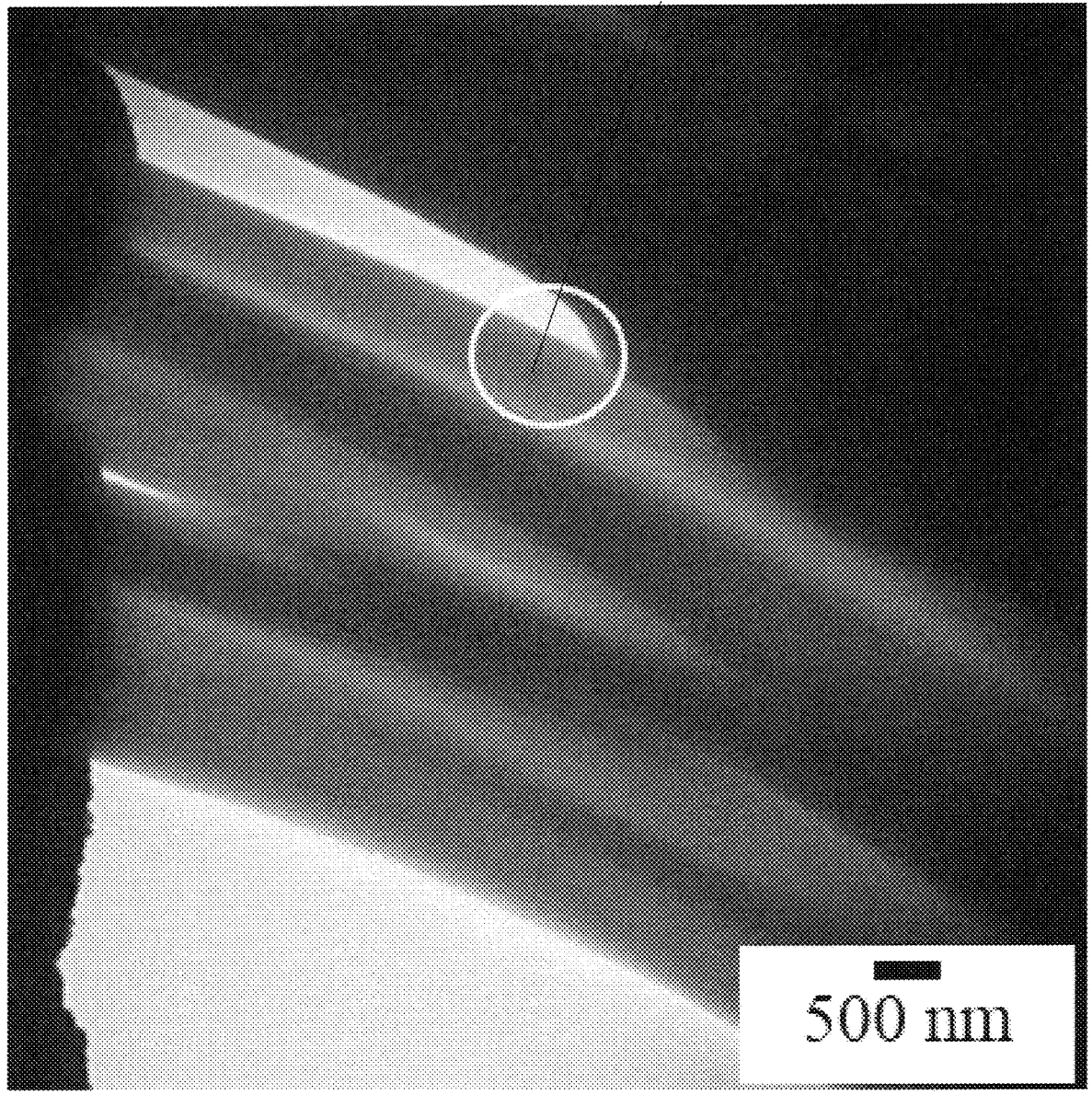
FIG. 5 is the transmission electron micrograph of FIG. 3B of coaxial or core-sheath fibers containing a virus at a lower magnification.

Preferred embodiments of the subject small-scale morphology materials of the subject invention are shown in FIGS. 3-5 and 8-9. Small scale materials may take on various structure seen in FIG. 3 (core-sheath fibers) versus FIG. 8 (single material fibers) and components may be oriented randomly or aligned or placed in a manner conducive to particle delivery. FIGS. 3-5_show a micro size polymer fiber with a core-sheath structure. A single fiber polymer shell casing 10 has a microfluidic channel 12 inside. Fibers were fabricated using coaxial electrospinning (ES). The microfluidic channel carries particles 16 (FIGS. 1 and 2) to be released.

The small scale morphology materials of the subject invention are for either the general, and/or intended, and/or specific delivery, movement, transfer, transport, or release of either particles, and/or particulate, and/or viruses. Particles can include, but are not limited to, molecules, viruses, phage, and natural or synthetic materials. Particles may be released to a living organism, innate surface, or artificial representation of either of these.

Particle/s and/or virus delivery from small scale morphology materials of the subject invention can be released from either the material matrix, and/or material surface, and/or material core. In the case that particles, and/or particulate, and/or viruses are delivered from a material core. The core refers to any layer more interior to that of the surface of the material which carries particles, and/or particulates, and/or viruses for delivery and can be of a material which differs from that found on the material surface or any layer more interior to the surface material. Particles for delivery via small scale morphology materials can be attached to fibers chemically, electrostatically, mechanically, or physically. Particles for delivery via small scale morphology materials may be released via active (with added energy) or passive means (without added energy). Particles for delivery via small scale morphology materials may be released immediately, or slowly over time, or a combination of these. More than one type of particle, either in composition, synthesis, chemistry, assembly, or appearance can be delivered via small scale morphology materials of the subject invention.

Small scale morphology materials used for either the transfer, transport, movement, delivery, or release of either particles, and/or particulate, and/or viruses, can consist of more than one material or of a single material. In the case that small scale morphology materials consist of more than one material, materials can differ in either chemical make-up, and/or consistency, and/or viscosity, and/or conductivity, and/or ion transfer ability, and/or amount.

Particles, and/or particulate, and/or viruses, and/or molecules, released from the subject material can be used for the treatment of disease, treatment of pain, sterilization of surfaces, manipulation of surface properties, filtration, energy harvesting, alteration of mechanical properties, adhesives, repellants, vaccines, preventative therapeutics, long-term implantation in eukaryotic organisms, manipulation of living system interactions, alteration of biological functions or processes, antibacterial agents, sensors, light manipulation, cosmetics, general and relaxation therapies, and cloak or disguise purposes.

Particles for release into living or non-living systems is carried out by small scale morphology materials of the subject invention. Particles can be attached to fibers via electrostatic, chemical, mechanical, or physical means and are released via energy requiring or passive means. Particles can include, but are not limited to, viruses and/or synthetic nanoparticles. When particles are embedded within a polymer material and are of other composition, the material is referred to as doped. Specifically, nanoparticle doped polymer fibers nanoparticles mixed in with the polymer melt or polymer mixed in solvent, and are then fed to a fabrication device such as an electrospinner for fiber construction. Resultant fibers would contain a polymer matrix but with nanoparticles of non-polymer origin as well. In the embodiment shown in FIGS. 3-5, where coaxial fibers were constructed for the purpose of virus 17 delivery. Coaxial electrospinning in this case, created a polymer sheath 10 with a water-based microfluidic core 12 for maintenance of the virus 17 to be delivered for antibacterial purposes. A combination of both of these examples could incorporate nanoparticle into polymer solution used for the protective sheath, and also contain virus in fluid as the fiber core material for nanoparticle assisted antibacterial therapy.

One or more particles are associated with the material of the subject invention. These particles can be attached to the exterior of small scale morphology materials, be contained within the small scale morphology material matrix, be contained within any layer more interior to the material surface, or be contained within a microfluidic channel.

Small scale morphology materials of the subject invention serve as delivery vehicles for particles from the material to living or non-living systems, or artificial representations of either of these. The subject material can move viruses in combination with or without nanoparticles from a polymer material to a living person for the purpose of antibiotic treatment. Nanoparticles in this case and in the case of other particulate release can serve as an adjuvant which enhances particle delivery and/or effectiveness upon successful transfer from small scale morphology materials to the intended living or non-living system, or artificial representation of these systems.

Example 1—Material Preparation

The small-scale morphology material of the subject invention can be fabricated using electrospinning technique. Electrospinning involves delivery of a polymer melt or polymer dissolved in solvent solution to a capillary or needle held above or horizontal to a collection plate. Polymers suitable for creating the small-scale morphology material of the subject invention include, but are not limited to, polycaprolactone, polyvinyl alcohol, polyethylene oxide, polystyrene, polyethylene oxide, PEDOT, PEDOT/PSS, polypropylene, and petadecylphenol. Voltage differential initiated between the tip of the capillary where polymer is being released and the collection plate surface creates a force which pulls the polymer solution or melt from the capillary tip, depositing micro- or nano-sized fibers or vesicles onto a collection plate.

The subject invention is meant to deliver particles; several methods may be used to equip these polymer delivery systems with particles for subsequent release: (1) particles can be pre-mixed with the polymer melt or polymer solution, (2) in the case of multiple layered materials such as core-sheath fibers created through coaxial electrospinning, particles may be incorporated into a core layer, microfluidic channel 12 (FIGS. 3-5), any layer other than the outermost layer, or any combination of layers, (3) particles may be added post-process via soaking in a solution filled with particles, electrospraying particles onto electrospun materials, creating an adhesive layer and adding dry particles, etc, or any combination of these methods. Iron-doped hydroxyapatite nanoparticles (IDANPs) have been used to enhance bacteriophage antibacterial properties, (see J. M. Andriolo et al., Iion-doped Apatitie Nanoparticles for Improvement of Phage Therapy, Journal of Vacuum Science and Technology B, 32(6), 2010.

Example 2—Particle Release

Figure 6:
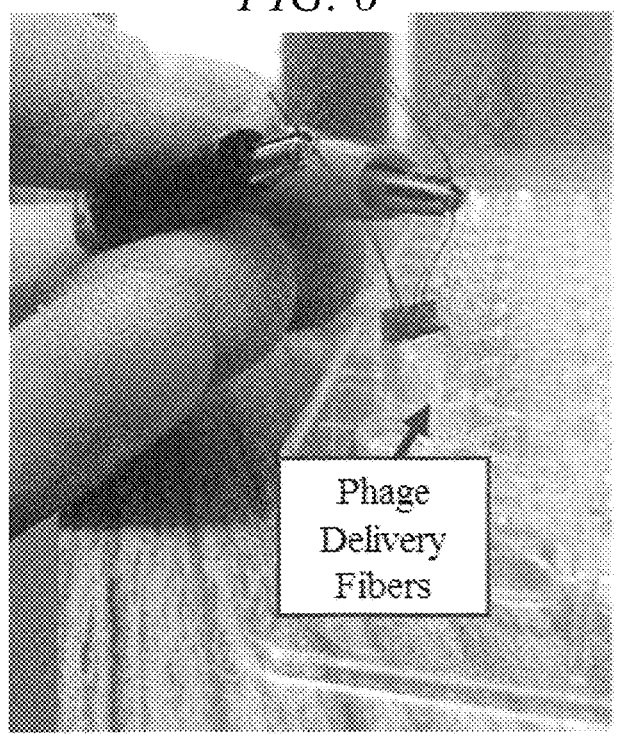
FIG. 6 is a photograph showing release of a particulate from a preferred embodiment of the small-scale morphology material of the subject invention by ohmic heating and melting of the material to release particles.
Figure 7:
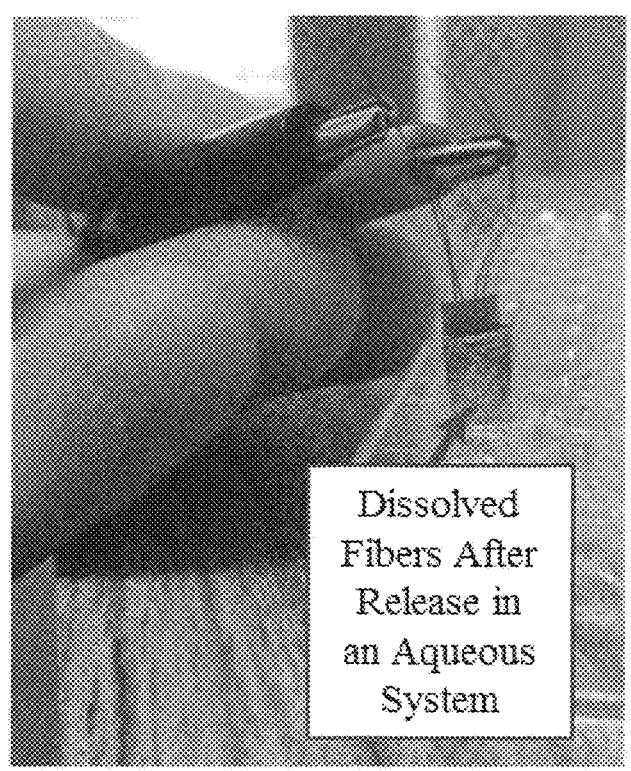
FIG. 7 is a photograph showing completed release of a particulate from the preferred embodiment of the small-scale morphology material.
Figure 8:
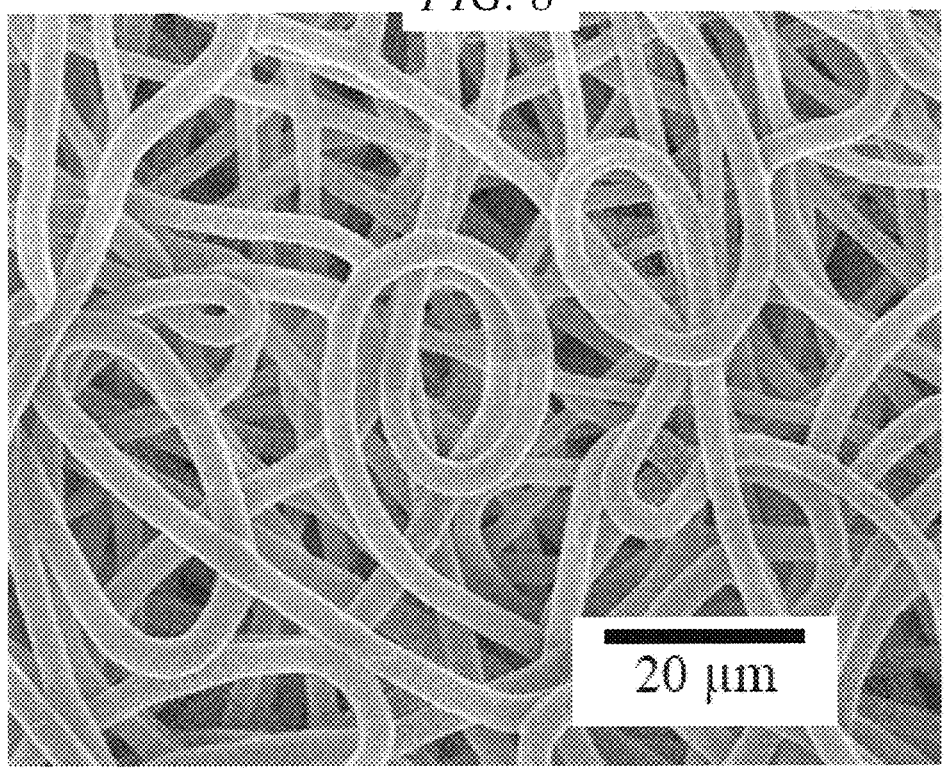
FIG. 8 is a scanning electron micrograph of another preferred embodiment of the small-scale morphology material of the subject invention that is non-coaxial or core-sheath.
Figure 9:
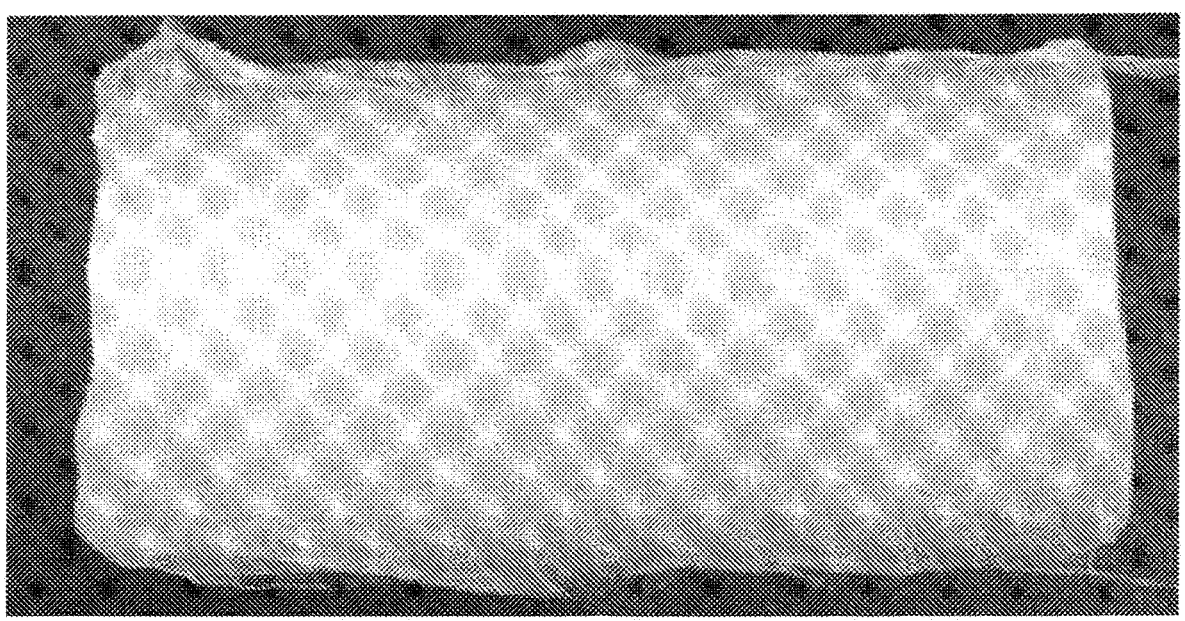
FIG. 9 is a photograph showing fibers from FIG. 4A on a macro scale that can be used to deliver particles or virus as the small scale-morphology material of the subject invention.

For subsequent delivery of particles from small scale morphology materials, several methods can be used. FIG. 6_demonstrates ohmic heating used to melt fibers for particle release. Melting of fibers or initiation of particle release from fiber surfaces can also be initiated externally using wireless charging devices, light, plasmonics, vibration, or magnetic sources or any source which alters material characteristics to allow for particle release. Upon release of particles, the material can itself dissolve into the living or non-living system for which it released to, or, may be removed and discarded.

IDANP Synthesis. Synthesis of IDANPs (FIG. 10) has been described previously [Andriolo et al., *Journal of Vacuum Science and Technology B*, 2013 & Andriolo et al., *IEEE Transactions on Nanobioscience*, 2016]. IDANPs resemble HA, a mineral that is well known to be biocompatible and most analogous to the inorganic constituent of mammalian bone and teeth (Palmer et al., *Chemical Reviews*, 2008). Such properties allow these NPs to serve as biocompatible adjuvants capable of entering a physiological system without significant immune system rejection. Previous synthesis investigations have accomplished the synthesis of citrate functionalized and/or dispersed IDANPs. The citrate ions complex with $Ca^{2+}$, and mediate the reaction leading to the formation of nanoapatite particles. The carboxylates of citrate, which at physiological pH are deprotonated, give rise to Coulombic repulsion in adjacent NPs. This repulsion causes dispersion and colloid formation. Lack of citrate results in elongate particles (FIG. 2). During synthesis, it was assumed that iron replaces calcium in the apatite unit cell to 30% iron in the ratio of total iron plus calcium. Lack of iron during synthesis results in elongated glass-like morphology of the particles. Citrate was used as a capping agent to arrest NPs at the nanoscale. Lack of citrate results in extended particle growth which resembles longer chains. The theoretical reaction formula is as follows:

$$7Ca(OH)_2 + 3FeCl_3 + 6KH_2PO_4 \xrightarrow{Citric\ Acid} Ca_7Fe_3(PO_4)_6(OH)_2 + 6KOH + 12H_2O + 9Cl^-$$

During synthesis of 30% IDANPs with 1× citrate, a 500 mL flask held at 25° C. was filled with 200 mL deionized water and stirred by stir bar as the following reagents were added in the order listed:

0.260 g Calcium Hydroxide (Ca(OH)2)
0.243 g Iron Chloride (FeCl3)
0.263 g Citric Acid Anhydrous (C6H7O7)
0.408 g monopotassium phosphate (KH2PO4) that was pre-dissolved in 50 mL deionized water is added dropwise over a period of 1 minute.

The final solution was measured at a pH of approximately 4.5 and brought up to a pH of 7.5 using 1 M NaOH. IDANPs were then stirred at 25° C. for seven days. After seven days, IDANPs were centrifuged for 30 min at 2000 rpm. IDANP supernatant was then removed, leaving the IDANP pellet. The pellet was washed 2× with sterile, deionized water (18 MΩ), and IDANPs were re-suspended in deionized water before being sterilized in an autoclave for 40 minutes. IDANP concentration resulting from this synthesis procedure was estimated to be 1.54 mg/mL by simple drying method and weighing of dried IDANPs. The addition of iron results in the bulk colloid solution appearing orange in color. IDANPs are approximately 20-50 nm in diameter once synthesis is completed.

Bacterial and Phage Maintenance. *Staphylococcus aureus* (ATCC® 33742, (FIG. 12) was maintained in long term storage at −80° C. before being plated on tryptic soy agar (4%) plates supplemented 1 mM calcium and 200 g/L dextrose (TSA++). Saturated cultures were acquired by growing the cells overnight in 3 mL tryptic soy broth with calcium and dextrose (TSB++) from a single colony. Prior to being used for plaque assays, saturated *S. aureus* culture was grown in a 1:100 dilution of TSA++ for 3 hr. Phage (FIG. 13) used during plaque assays were discovered on dairy cow hair samples at Montana State University, and isolated on methicillin-resistant *S. aureus* strain USA300. Phage stocks were stored at 4° C. at a concentration of 109 PFU/mL.

Figure 14:
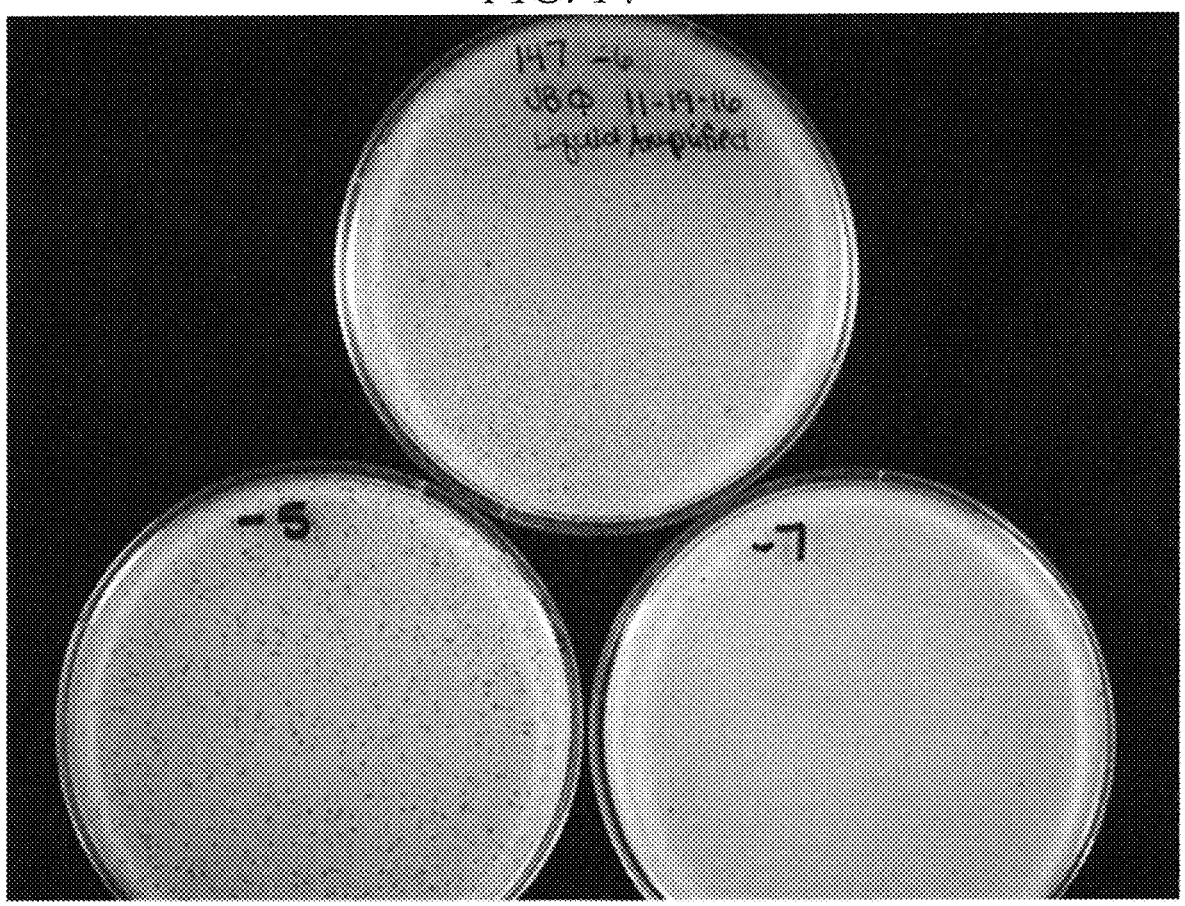
FIG. 14 In plaque assays, bacteria are grown over the surface of an agar plate, forming a bacterial "lawn" or layer which completely coats the surface. Phage which are added to bacteria infect and kill the bacterial cells, thereby forming small vacancies in the bacteria layer where bacteria have lysed.

Plaque Assays for Efficacy Testing of IDANP- and Phage-Filled Polymer Materials. Plaque assays (FIG. 14) were used to test phage release from polymer fibers. In plaque assays, the surface of an agar plate is completely covered in bacterial grown, forming one solid layer on top of the agar. In plaque assays, phage infect and kill bacteria cells, forming circular vacancies in the bacterial layer. Such circular vacancies are termed "plaques," and are reported in concentrations of plaque forming units per mL (PFU/mL). Coaxial ES fibers containing phage were agitated in a shaker at 225 rpm and at 37° C. (physiological temperature) in mammalian media (minimal essential media with 10% fetal bovine serum and 1% penicillin-streptomycin antibiotic) for 1 hr. During the 1 hr time period, aliquots of the mammalian media was removed at 15 min increments and serial diluted into TSA++. Serial dilutions of the phage were then placed in separate test tubes containing 250 μL *S. aureus*, allowing the phage to infect *S. aureus* for 10 min. Following infection, the treated and infected bacteria were mixed with a 1:1 mixture of tryptic soy top agar (0.7%) and TSA++, and poured onto TSA++ plates (4%). TSA++ plates were then allowed to solidify in ambient conditions before overnight incubation at 37° C. A subsequent plaque assay was also performed at 24 hr agitation at physiological temperature. Plaque assays are performed in triplicate.

IDANP-Filled Polymer Preparation and Electrospinning. IDANPs were centrifuged at 2,000 RPM for 10 min and supernatant fluid removed prior to being placed PEO polymer by simple mixing with a magnetic stir bar on stir plate. PEO (Mv 400,000) was dissolved in methanol and water (14:1). IDANP concentration in final prepared polymer was 2.03 mg/mL. Polymer was delivered to the spinneret (24 gauge) at a rate of 0.4 mL/hr, and ES was initiated at a voltage of 14 kV, and brought down to 10.5 kV for stable ES. Separation distance was 7.62 cm. IDANP release from PEO fibers (FIG. 15-18) and subsequent effect on phage killing of bacteria was tested via plaque assay and results are shown in FIG. 19.

Figure 23:
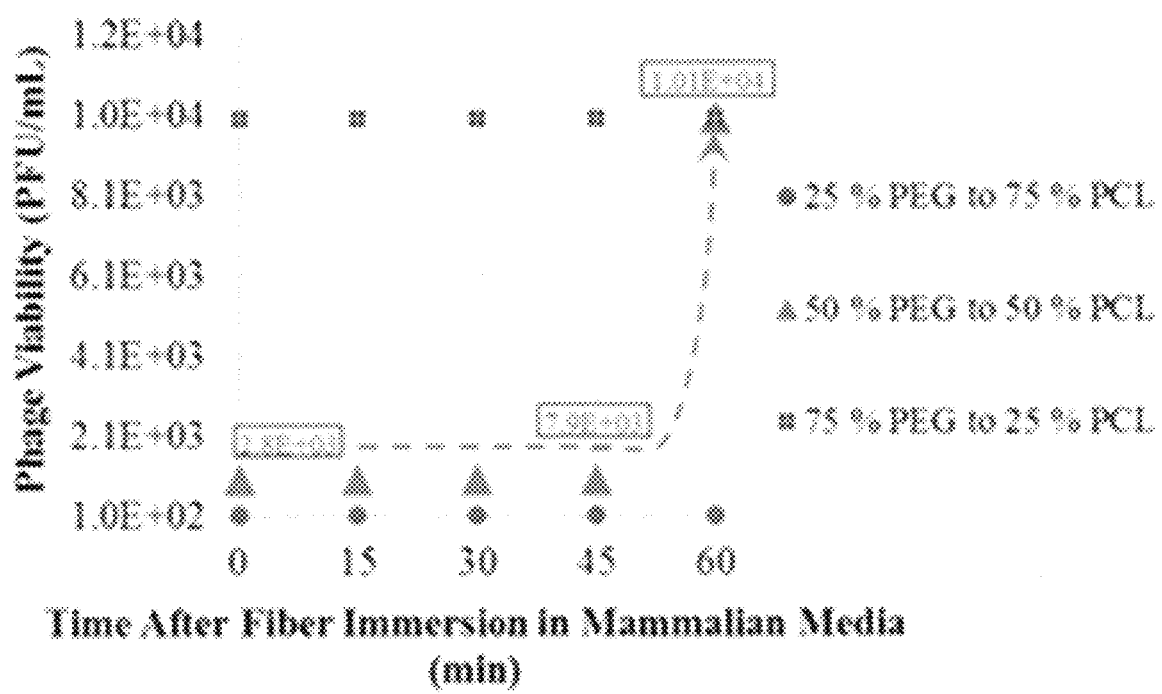
FIG. 23 In plaque assays, the mostly insoluble polymer mix fibers (3:1 PCL to PEG) released phage but at an exponential loss of viability, which did not increase over the 1 hr time period tested. The mostly soluble polymer mix fibers (1:3 PCL to PEG) released phage at a maximum immediately, which did not change over the 1 hr time period. The polymer blend mix of 1:1 PCL to PEG revealed a release profile which increased from $10^3$ PFU/mL to $10^4$ PFU/mL over the 1 hr time period, which was ideal for the IDANP-assisted phage therapy treatment mesh desired.

Phage-Filled Polymer Preparation and Electrospinning. Blended polymers for ES were prepared at various wt % in chloroform by mixing with a stir bar on stir plate over low heat. PCL (80,000 MW) was blended with PEG (8,000 MW) for controlled release of phage. During ES, a coaxial spinneret with an inner gauge diameter of 26, and outer gauge diameter of 20 was used to form coaxial (core-sheath) structured fibers containing phage in a microfluidic core (FIGS. 20-22). Separation distance was 6 cm, ES was performed at 11-15 kV, polymer was fed into the electrospinner at 1.5 mL/hr, and phage solution was fed into the fiber core at 0.5 mL/hr. Phage release from PCL/PEG blend polymer fibers was tested via plaque assay and results are shown in FIG. 23. The mostly insoluble polymer mix fibers (3:1 PCL to PEG) released phage but at an exponential loss of viability, which did not increase over the 1 hr time period tested. The mostly soluble polymer mix fibers (1:3 PCL to PEG) released phage at a maximum immediately, which did not change over the 1 hr time period. The polymer blend mix of 1:1 PCL to PEG revealed a release profile which increased from $10^3$ PFU/mL to $10^4$ PFU/mL over the 1 hr time period, which was ideal for the IDANP-assisted phage therapy treatment mesh desired.

IDANPs have demonstrated a unique influence over phage infection and killing of bacteria cells, in which IDANP-exposed bacterial cultures experience up to 2× the bacterial death as compared to controls (Andriolo et al., *Journal of Vacuum Science and Technology B*, 2013). As antibacterial resistance to mainstream antibiotics increases (Centers for Disease Control and Prevention, 2013), phage have been suggested as an alternative antibiotic therapy. IDANPs are composed of HA, a material found in mammalian bones and teeth and used in many FDA approved medical applications (Palmer et al., *Chemical Reviews*, 2008 & Hench, *Journal of the American Ceramic Society*, 1998). The potential biocompatibility of IDANP's, coupled with the functionality of these NPs as an aid to an alternative antibiotic therapy, make them of interest for medical applications. For controlled release of an IDANP-assisted phage therapy treatment for bacterial infections, a delivery system was designed, in which, IDANPs and phage are encased in micro-scale (at least one component with dimension less than 1,000 µm) polymer materials.

It is understood that the foregoing examples are merely illustrative of the present invention. Certain modifications of the articles and/or methods may be made and still achieve the objectives of the invention. Such modifications are contemplated as within the scope of the claimed invention.

What is claimed is:

1. A particle delivery system comprising:
An electrospun nanofiber composite mesh comprised of a first rapid release layer of a first nanofiber, wherein said first nanofiber is comprised of iron doped apatite nanoparticles (IDANPs) and a second slow-release layer comprised of a second nanofiber, wherein said second nanofiber is a coaxial fiber with a microfluidic core, wherein a second particle is contained within said microfluidic core.

2. The particle delivery system of claim 1 where said electrospun nanofiber composite mesh is further comprised of a superficial, rapid release layer of polyethylene oxide (PEO) fibers.

3. The particle delivery system of claim 2 where said polyethylene oxide (PEO) fibers are doped with IDANPs.

4. The particle delivery system of claim 2 where said coaxial fibers are located deeper than said superficial, rapid release layer of polyethylene oxide (PEO) fibers.

5. The particle delivery system of claim 4 where said coaxial fibers are comprised of polycaprolactone/polyethylene glycol (PCL/PEG) blended polymer.

6. The particle delivery system of claim 1 where any particle is contained within said microfluidic core.

7. The particle delivery system of claim 1 where phage are contained within said microfluidic core.

8. The particle delivery system of claim 1 where virus are contained within said microfluidic core.

9. The particle delivery system of claim 3 where IDANP concentration of said polyethylene oxide (PEO) fibers is 2.03 mg/mL.

10. The particle delivery system of claim 1 where said second particle is comprised of phage.

11. The particle delivery system of claim 2 where said second particle is comprised of phage.

12. The particle delivery system of claim 1 where said electrospun nanofiber is applied to bacteria.

13. The particle delivery system of claim 1 where said electrospun nanofiber composite mesh is applied to a bacterial infection of a mammalian system.

14. The particle delivery system of claim 1 where said electrospun nanofiber is applied topically to a bacterial infection of a mammalian system.

15. The particle delivery system of claim 1 where said electrospun nanofiber is applied to food products to prevent bacterial contamination.

* * * * *